US012447108B2

(12) United States Patent
Euvrard et al.

(10) Patent No.: US 12,447,108 B2
(45) Date of Patent: Oct. 21, 2025

(54) ADAPTOR FOR A MEDICAL CONTAINER AND A MEDICAL CONTAINER COMPRISING SAID ADAPTOR

(71) Applicant: Becton Dickinson France, Le Pont-de-Claix (FR)

(72) Inventors: Nicolas Euvrard, Plainsboro, NJ (US); Cédric Rivier, Voreppe (FR)

(73) Assignee: Becton Dickinson France, Le Pont-de-Claix (FR)

(*) Notice: Subject to any disclaimer, the term of this patent is extended or adjusted under 35 U.S.C. 154(b) by 319 days.

(21) Appl. No.: 17/800,327

(22) PCT Filed: Feb. 16, 2021

(86) PCT No.: PCT/EP2021/053760
§ 371 (c)(1),
(2) Date: Aug. 17, 2022

(87) PCT Pub. No.: WO2021/165254
PCT Pub. Date: Aug. 26, 2021

(65) Prior Publication Data
US 2023/0062851 A1 Mar. 2, 2023

(30) Foreign Application Priority Data
Feb. 18, 2020 (EP) .................................... 20305150

(51) Int. Cl.
*A61J 1/20* (2006.01)
*A61M 39/10* (2006.01)

(52) U.S. Cl.
CPC ........ *A61J 1/2055* (2015.05); *A61M 39/1011* (2013.01); *A61M 2039/1077* (2013.01); *A61M 2205/581* (2013.01); *A61M 2205/582* (2013.01)

(58) Field of Classification Search
CPC .. A61J 1/2055; A61J 2205/40; A61J 2205/70; A61J 1/2065; A61J 1/2096;
(Continued)

(56) References Cited

U.S. PATENT DOCUMENTS 4,994,029 A * 2/1991 Rohrbough ......... A61M 5/2429 215/DIG. 8
9,233,776 B2 * 1/2016 Bazala .................. A61J 1/2096
(Continued)

FOREIGN PATENT DOCUMENTS

CN 105873558 A * 8/2016 .............. A61J 1/201
EP 2666513 A1 11/2013
(Continued)

*Primary Examiner* — Rebecca E Eisenberg
*Assistant Examiner* — Matthew Wrubleski
(74) *Attorney, Agent, or Firm* — The Webb Law Firm

(57) ABSTRACT

An adaptor for connecting a medical container to a connector, the adaptor including longitudinal projections including a distal portion configured to exert a progressively increasing radial pressure on connecting means of the connector when said connector is moved axially proximally within the adaptor and a proximal portion configured to authorize the partial release of said pressure as the connector is moved further proximally, said proximal portion being further configured to be contacted by said connecting means upon said partial release of said pressure and to emit a sound when contacted by said connecting means, thereby providing an end user with a tactile and audible indication that the connection between the connector and the adaptor is secured. The disclosure also relates to a medical container having such an adaptor mounted onto its distal tip.

7 Claims, 2 Drawing Sheets

(58) Field of Classification Search
CPC ...... A61M 39/1011; A61M 2039/1077; A61M 2205/581; A61M 2205/582
See application file for complete search history.

(56) References Cited

U.S. PATENT DOCUMENTS

| | | | | |
|---|---|---|---|---|
| 10,278,897 | B2 * | 5/2019 | David ................... | A61J 1/2013 |
| 10,799,423 | B2 * | 10/2020 | Sund ..................... | A61J 1/2096 |
| 2002/0127150 | A1 | 9/2002 | Sasso | |
| 2005/0209553 | A1 | 9/2005 | Landau | |
| 2019/0298986 | A1 | 10/2019 | Rivier et al. | |

FOREIGN PATENT DOCUMENTS

| | | | |
|---|---|---|---|
| EP | 3202390 | A1 * | 8/2017 |
| EP | 3269418 | A1 | 1/2018 |

* cited by examiner

ADAPTOR FOR A MEDICAL CONTAINER AND A MEDICAL CONTAINER COMPRISING SAID ADAPTOR

CROSS REFERENCE TO RELATED APPLICATIONS

This application is the United States national phase of International Application No. PCT/EP2021/053760 filed Feb. 16, 2021, and claims priority to European Patent Application No. 20305150.3 filed Feb. 18, 2020, the disclosures of which are hereby incorporated by reference in their entirety.

BACKGROUND OF THE DISCLOSURE

Field of the Disclosure

The present disclosure relates to an adaptor for connecting a medical container to a connector and to a medical container comprising said adaptor.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to an adaptor or a medical container of the disclosure, and the "proximal direction" is to be understood as meaning the opposite direction to said direction of injection, that is to say the direction towards the user's hand holding a medical container as for an injection operation.

Basically, the medical container, such as for example a syringe, usually comprises a container forming a reservoir for containing a medical product. The container has a distal end in the form of a longitudinal tip defining an axial passageway through which the medical product is expelled from the container. However, this longitudinal tip does not allow parenteral administration by itself and must either comprise a staked needle or an adaptor allowing the connection of the syringe to a connector such as a needle hub.

DESCRIPTION OF RELATED ART

It is important that the connector engages the distal end of the container correctly in order to establish a safe fluid path between the reservoir and said connector.

Numerous connections of a connector to an adaptor are performed by screwing the connector into the adaptor. In such a case, it is important that the connector be properly screwed into the adaptor. The end user has to apply a sufficient torque when screwing the connector into the adaptor in order to get a proper fitting of the connector onto the distal end of the container. Under screwing into the adaptor may otherwise lead to an ejection of the connector or a leakage when transferring a fluid between the container and the connector, the leakage occuring between the connector and the tip of the syringe. Alternatively, over screwing of the connector into the adaptor may lead to the rotation or tilt of the adaptor.

Another way of connecting a connector to an adaptor is to perform an axial connection between the connector and the adaptor, for example by way of a snap fit connection. It is nevertheless desirable in such cases also to ensure that the connector is correctly connected to the adaptor, i.e. that the connector is at an axial position in the adaptor allowing a fluid communication between the distal tip of the medical container and the connector.

There is therefore a need for a medical container providing the end user with an indication that the connector is correctly connected to the adaptor and thus improving the end user confidence during a connection and an injection step.

SUMMARY OF THE DISCLOSURE

An aspect of the disclosure is an adaptor for connecting a medical container to a connector having a proximal region provided with connecting means at its proximal end, the adaptor comprising

- a proximal part configured to be secured onto a distal tip of a medical container,
- a distal part configured to receive said proximal region of said connector in order to establish a fluid communication between the distal tip of the medical container and the connector,
- a plurality of projections configured to engage said connecting means in an axial snap fit relationship when the connector reaches a predetermined position in the adaptor,
- the plurality of longitudinal projections being distributed circumferentially on an inner surface of said distal part,
- the longitudinal projections comprising a distal portion configured to exert a progressively increasing radial pressure on said connecting means as the connector is moved axially proximally within the adaptor and a proximal portion configured to authorize the partial release of said pressure as the connector is moved further axially proximally, said proximal portion being further configured to be contacted by said connecting means upon said partial release of said pressure and to emit a sound when contacted by said connecting means, thereby providing an end user with a tactile and audible indication that the connection between the connector and the adaptor is secured,
- wherein the distal portion of the longitudinal projections comprises a first wall having a first radial thickness, the value of said first radial thickness increasing from a distal end of said distal portion to a proximal end of said distal portion, and
- wherein the proximal portion of the longitudinal projections comprises a second wall having a substantially constant second radial thickness, the value of said second radial thickness being greater than the value of said first radial thickness at the distal end of said distal portion and being less than the value of said first radial thickness at the proximal end of said distal portion.

In particular, said predetermined position to be reached by the connector in the adaptor may correspond to a predetermined depth of the connecting means in the adaptor. Said predetermined depth is defined as being the depth above which there is no leaks. The leakage limit may be defined by the ISO 80369-7 of 2016, paragraphs 6.1 and 6.2. At such a predetermined position, the connection between the connector and the adaptor is secured.

The adaptor of the disclosure thus permits the end user to be informed that the connection between the connector and the adaptor is correctly completed and that the risks of leakage or of an ejection of the connector during a fluid transfer are avoided. The structure of the longitudinal projections of the adaptor requires that the end user provides an increasing effort until the connecting means of the connector reach the proximal portions of these longitudinal projections, where an effort is no longer required. This consequently gives to the end user a tactile and audible indication that the connection is correctly performed and terminated. In addition, this also improves the end user confidence during the connection step and the injection step.

By "a plurality" is meant according to the present application "at least two".

In an embodiment, the longitudinal projections are regularly distributed circumferentially on the inner surface of said distal part of the adaptor. For example, the plurality of longitudinal projections may comprise at least two, preferably at least four, longitudinal projections regularly distributed circumferentially on the inner surface of said distal part. In embodiments, the plurality of longitudinal projections comprise six longitudinal projections regularly distributed circumferentially on the inner surface of said distal part. This helps ensuring that the connecting means of the connector extend circumferentially on a distance strictly greater than the space left between two adjacent longitudinal projections. The disconnection of the connector from the adaptor, by way of the connecting means of the connector escaping from the longitudinal projections, is therefore made impossible.

The distal portion of the longitudinal projections comprises a first wall having a first radial thickness, the value of said first radial thickness increasing from a distal end of said distal portion to a proximal end of said distal portion. Such a structure causes the end user to apply an increasing effort as he moves the connector proximally within the adaptor in order to perform the connection.

The proximal portion of the longitudinal projections comprises a second wall having a substantially constant second radial thickness, the value of said second radial thickness being greater than the value of said first radial thickness at the distal end of said distal portion and being less than the value of said first radial thickness at the proximal end of said distal portion.

This allows the connecting means of the connector to contact the proximal portion of the adaptor with a force sufficient to produce a significant sound allowing the end user to be informed that the connector has reached the correct position in the adaptor. This also allows a sudden change in the effort that needs to be provided by the end user. Indeed, once the connecting means of the connector have reached the proximal portion of the longitudinal projection, no more effort is required from the end user. This drop in the necessary effort also provides the end user with a tactile indication that the connection is correctly performed.

In embodiments, said second wall of the proximal portion of the longitudinal projection shows a circumferential width W2 lower than a circumferential width W1 of said first wall of the distal portion of the longitudinal projection. Typically, the circumferential width W2 is about half of the circumferential width W1. Preferably, $W1>W2\geq 0.5W1$.

Typically, the connector comprises at least two connection means, preferably exactly two connection means. Preferably the connection means of the connector are outer wings.

Another aspect of the disclosure is a medical container comprising a distal tip and the adaptor described above, said adaptor being mounted onto the distal tip of the medical container.

Another aspect of the disclosure is a method for manufacturing the adaptor above, said method comprising the step of forming the adaptor by injection molding.

BRIEF DESCRIPTION OF THE DRAWINGS

The disclosure and the advantages arising therefrom will clearly emerge from the detailed description that is given below with reference to the appended drawings as follows.

DETAILED DESCRIPTION

Figure 1:
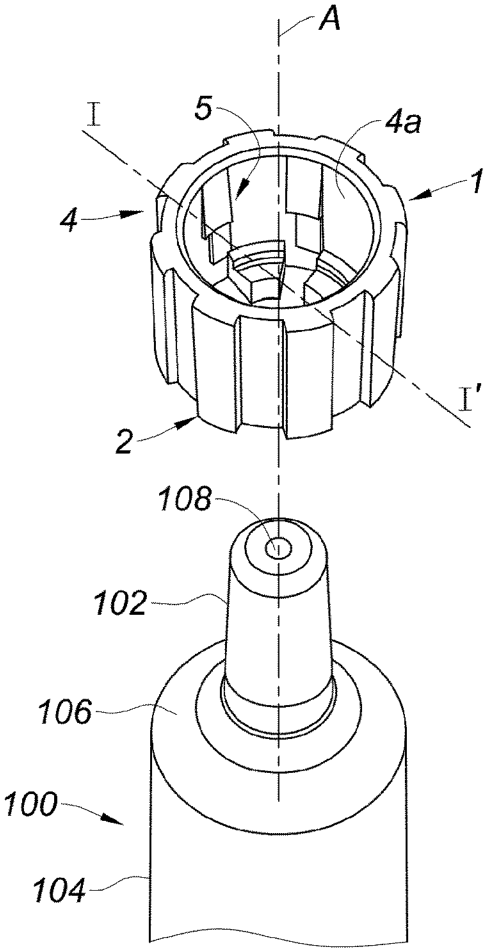
FIG. 1 is a perspective view of an adaptor according to an embodiment of the disclosure and of the distal tip of a medical container intended to receive said adaptor.
Figure 2:
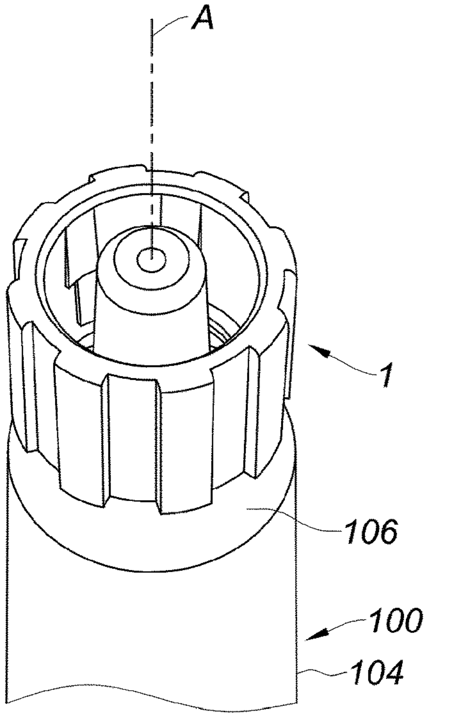
FIG. 2 is a perspective view of the adaptor and medical container of FIG. 1, where the adaptor is mounted onto the distal tip of the container.

With reference to FIG. 1 is shown an adaptor 1 according to an embodiment of the disclosure. With reference to FIGS. 1 and 2, the adaptor 1 is intended to be mounted onto the distal tip 102 of a medical container 100, in particular onto the outer surface of the distal tip 102. The outer surface of the distal tip 102 is generally distally tapered or frustoconical. Alternatively, it could be cylindrical. The adaptor 1 permits to connect a connector, such as a needle hub 200 see FIG. 4) having a proximal region 201 provided with connecting means, such as two outer wings 202, at its proximal end, to the distal tip 102.

With reference to FIGS. 1-4, the adaptor 1 comprises a proximal part 2, which may be in the form of a mounting ring, configured to be secured to the medical container 100, and a distal part 4, which may be in the form of a connecting ring, configured to receive the connector in order to establish a reliable fluid communication between a passageway of the distal tip 102 and the connector.

The connector, such as the needle hub 200, is intended to be axially connected to the adaptor 1 in a snap fit relationship.

In this view, the adaptor 1 has a plurality of longitudinal projections 5 configured to engage the outer wings 202 of the needle hub 200 in an axial snap fit relationship when the needle hub 200 reaches a predetermined position in the adaptor 1, said predetermined position being the position where the connection between the needle hub 200 and the distal tip 102 of the medical container 100 is secured and a reliable fluid communication between the needle hub 200 and the distal tip 102 is ensured. Said position is also defined as being the limit depth above which there is no leak. The leakage limit may be defined by the ISO 80369-7 of 2016, paragraphs 6.1 and 6.2.

Figure 3:
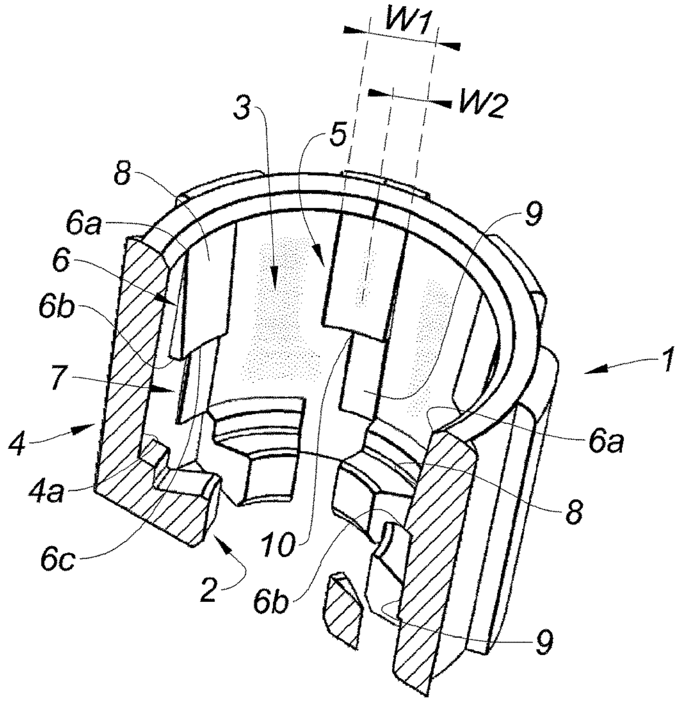
FIG. 3 is a cross section perspective view of the adaptor taken along plane I-I' of FIG. 1.

With reference to FIGS. 1-3, the plurality of longitudinal projections 5 is distributed circumferentially on the inner surface 4*a* of the distal part 4 of the adaptor 1.

The longitudinal projections 5 comprise a distal portion 6 and a proximal portion 7. The distal portion 6 is configured to exert a progressively increasing radial pressure on the outer wings 202 of the needle hub 200 when the needle hub 200 is moved proximally within the adaptor 1. In the example shown, the distal portion 6 comprises a first wall 8. This first wall 8 has a first radial thickness the value of which varies from the distal end 6*a* of the distal portion 6 to the proximal end 6*b* of this distal portion 6. In particular, the value of the first radial thickness increases from the distal end 6*a* of the distal portion 6 to the proximal end 6*b* of this distal portion 6.

The proximal portion 7 is configured to authorize the partial release of the radial pressure exerted on the outer wings 202 of the needle hub 200 as the needle hub 200 is further moved proximally within the adaptor 1. The proximal portion 7 is further configured to be contacted by the outer wings 202 upon the release of said radial pressure and to emit a sound when contacted by said outer wings 202. In the example shown, the proximal portion 7 comprises a second wall 9. The second wall 9 has a second radial thickness, which may be substantially of constant value. The value of the second radial thickness is preferably less than the value of the first radial thickness at the proximal end 6*b* of the distal portion 6. This allows the radial pressure exerted on the outer wings 202 of the needle hub 200 to be released when the needle hub 200 is moved in the direction of the proximal part 2 of the adaptor 1 as well as ensuring that the outer wings 202 produce a sound when they contact the second wall 9 upon the release of said radial pressure.

In particular, the value of the second radial thickness is less than the value of the first radial thickness at the proximal end 6*b* of the distal portion 6 and greater than the value of the first radial thickness at the distal end 6*a* of the distal portion 6. Typically, the value of the second radial thickness of the second wall is about half of the value of the first radial thickness at the proximal end 6*b*. This allows firmly maintaining the outer wings 202 in abutment against the second wall 9, thereby ensuring that the needle hub 200 is firmly engaged in a snap fit relationship in the adaptor 1, with no possibility that the needle hub 200 moves and/or rotate within the adaptor 1.

With reference to FIG. 3, the second wall 9 has a circumferential width W2 which is lower than the circumferential width W1 of the first wall 8. Typically, the circumferential width W2 is about half of the circumferential width W1. Preferably, $W1>W2\geq 0.5W1$.

The longitudinal projections 5 are preferably regularly distributed on a circumference of the inner surface of the distal part 4 of the adaptor 1. The number of longitudinal projections 5 is preferably above two, for example from three to ten, in order to ensure a safe maintaining of the needle hub 200 within the adaptor 1. The number of longitudinal projections 5 may be four. In the example shown on the figures the number of longitudinal projections 5 is six. As will appear from the description of FIG. 4, such a number of longitudinal projections 5 allows ensuring that the two outer wings 202 of the needle hub 200 extend circumferentially on a distance greater than the interspaces 3 between two adjacent longitudinal projections 5. As a result, once the needle hub 200 is axially engaged in the adaptor 1 as described above, it may not be removed therefrom, the proximal face 6*c* see FIG. 3) of the distal portion 6 forming an abutment surface preventing the outer wing 202 to be moved in the distal direction.

The adaptor 1 may be made of a plastic material, more precisely of any rigid polymer adapted to medical use, such as high density polyethylene PE), polypropylene PP), polycarbonate PC), acrylonitrile butadiene styrene ABS), polyoxymethylene POM), polystyrene (PS), polybutylene terephthalate PBT), polyamide PA), and combinations thereof. Preferably, the adaptor 1 is made of polycarbonate PC).

The adaptor 1 may be manufactured by injection molding using two different inserts.

Figure 4:
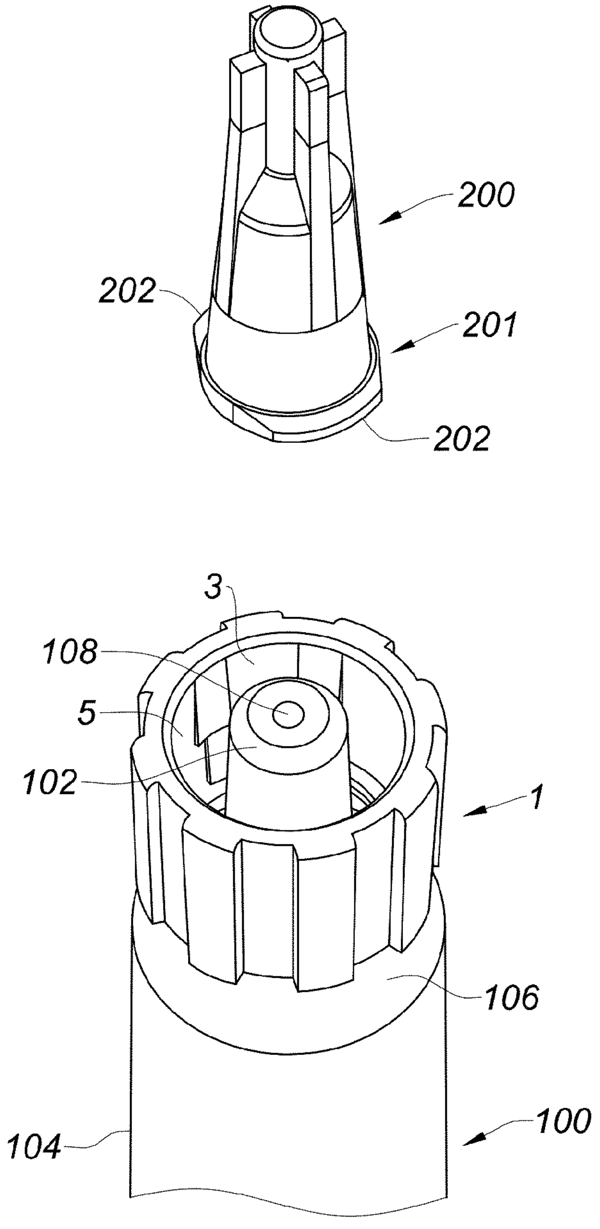
FIG. 4 is a perspective view of the adaptor mounted onto the distal tip of the medical container of FIG. 2 about to receive a needle hub.

With reference to FIGS. 1-2 and 4, the disclosure also relates to a medical container 100 comprising a distal tip 102 and an adaptor 1 having the above described features, said adaptor 1 being mounted onto the distal tip 102 of the medical container 100. The medical container 100, which may be a syringe, such as pre fillable or prefilled syringe, comprises a tubular barrel 104 that defines a reservoir for a medical product. The tubular barrel 104 is provided with the distal tip 102 that may protrude from a distal shoulder 106. The distal tip 102 may be cylindrical or distally tapered or frustoconical. The distal tip 102 includes an internal passageway 108 in communication with the reservoir. The tubular barrel 104 and the distal tip 102 may be made of glass or of plastic material. The medical container 100 may be provided with a piston and a plunger rod not shown) so as to expel the medical product from the reservoir and through the passageway 108. The adaptor 1 may be secured to the distal tip 102 by gluing, screwing, friction force or snap fitting.

The operation of the adaptor 1 is described herein below with reference to FIGS. 3 and 4.

The user inserts the needle hub 200 axially into the distal end of the adaptor 1. In the example shown, the outer wings 202 extend circumferentially on a distance greater than the interspaces 3 as defined above. The user may therefore insert the outer wings 202 within the adaptor 1 without having to care about the orientation of the outer wings 202 with respect to the longitudinal projections 5. As the needle hub 200 is moved in the proximal direction, the outer wings 202 contact the first wall 8. Because of the increasing of the first radial thickness of the first wall 8, the radial pressure exerted onto the outer wings 202 increases as the needle hub 200 is further moved proximally. The outer wings 202 are therefore progressively squeezed and deformed in the inward radial direction. The user feels that he has to apply an increasing effort in order to insert the needle hub 200 into the adaptor 1. Once the outer wings 202 reach the proximal end 6*b* of the first wall 8, the radial pressure exerted on the outer wings 202 is at its peak, and further proximal movement of the needle hub 200 with respect to the adaptor 1 causes partial release of the radial pressure on the outer wings 202, which expand until they contact the second wall 9. The needle hub 202 has reached the predetermined position in which the connection between the needle hub 200 and the distal tip 102 is secured. When contacting the second wall 9, the outer wings 202 produce a sound that informs the user that the connection is correctly performed, and thus secured. Moreover, the drop in the necessary axial effort further allows the user to be informed that the connection is performed. The longitudinal projections 5 therefore provide both a tactile indication and an audible indication that the connection is safely performed.

The adaptor of the disclosure allows therefore improving the end user confidence during connection and injection.

The invention claimed is:

1. An adaptor for connecting a medical container to a connector having a proximal region provided with connecting means at its proximal end, the adaptor comprising:

a proximal part configured to be secured onto a distal tip of a medical container, a distal part configured to receive said proximal region of said connector in order to establish a fluid communication between the distal tip of the medical container and the connector, the distal part comprising a circumferential wall with an axial length, wherein the circumferential wall is continuous throughout the axial length, a plurality of longitudinal projections configured to engage said connecting means in an axial snap-fit relationship when the connector reaches a predetermined position in the adaptor, the plurality of longitudinal projections being distributed circumferentially on an inner surface of said distal part, the longitudinal projections comprising a distal portion configured to exert a progressively increasing radial pressure on said connecting means as the connector is moved axially proximally within the adaptor and a proximal portion configured to authorize the partial release of said pressure as the connector is moved further axially proximally, said proximal portion being further configured to be contacted by said connecting means upon said partial release of said pressure and to emit a sound when contacted by said connecting means, thereby providing an end user with a tactile and audible indication that the connection between the connector and the adaptor is secured, wherein the distal portion of the longitudinal projections comprises a first wall having a first radial thickness, the value of said first radial thickness increasing from a distal end of said distal portion to a proximal end of said distal portion, wherein the proximal portion of the longitudinal projections comprises a second wall having a substantially constant second radial thickness, the value of said second radial thickness being greater than the value of said first radial thickness at the distal end of said distal portion and being less than the value of said first radial thickness at the proximal end of said distal portion, and wherein the circumferential wall has, outside of the longitudinal projections, a third radial thickness that is less than the value of the second radial thickness such that the second wall of the proximal portion of the longitudinal projections protrudes inwardly from the inner surface of the circumferential wall.

2. The adaptor according to claim 1, wherein the longitudinal projections are regularly distributed circumferentially on the inner surface of said distal part.

3. The adaptor according to claim 1, comprising at least four longitudinal projections regularly distributed circumferentially on the inner surface of said distal part.

4. The adaptor according to claim 1, comprising six longitudinal projections regularly distributed circumferentially on the inner surface of said distal part.

5. The adaptor according to claim 1, wherein said second wall being a circumferential width W2 lower than a circumferential width W1 of said first wall.

6. A medical container comprising a distal tip and the adaptor according to claim 1, said adaptor being mounted onto the distal tip of the medical container.

7. A method for manufacturing the adaptor according to claim 1, said method comprising the steps of forming the adaptor by injection molding.

* * * * *